United States Patent [19]

Sweet et al.

[11] Patent Number: 4,840,796

[45] Date of Patent: Jun. 20, 1989

[54] BLOCK COPOLYMER MATRIX FOR TRANSDERMAL DRUG RELEASE

[75] Inventors: Randall P. Sweet; Chi-long Lee; Gerald A. Gornowicz, all of Midland, Mich.

[73] Assignee: Dow Corning Corporation, Midland, Mich.

[21] Appl. No.: 184,748

[22] Filed: Apr. 22, 1988

[51] Int. Cl.$^4$ .............................................. A61F 13/02
[52] U.S. Cl. .................................... 424/448; 424/449; 424/484; 424/486
[58] Field of Search ................. 424/448, 449, 484, 486

[56] References Cited

U.S. PATENT DOCUMENTS

| | | | |
|---|---|---|---|
| 3,598,122 | 8/1971 | Zaffaroni | 424/448 X |
| 4,435,180 | 3/1984 | Leeper | 604/896 |
| 4,559,054 | 12/1985 | Bruck | 424/449 X |
| 4,615,699 | 10/1986 | Gale | 424/449 X |
| 4,638,043 | 1/1987 | Szycher et al. | 424/449 X |
| 4,690,683 | 9/1987 | Chien et al. | 424/449 X |

FOREIGN PATENT DOCUMENTS

| | | | |
|---|---|---|---|
| 59/084817 | 5/1984 | Japan | 424/449 |
| 2081582 | 2/1982 | United Kingdom | 424/449 |

*Primary Examiner*—Thurman K. Page
*Attorney, Agent, or Firm*—Allan O. Maki

[57] ABSTRACT

A transdermal drug delivery system, is provided which includes, in combination, an impermeable backing member, a matrix containing a medicinally active ingredient, and a pressure sensitive adhesive for affixing the system to the skin of a patient; the improvement in such system is based on the fact that said matrix is drug permeable (including to hydrophilic drugs) and is formed of a copolymer which can be softened sufficiently at temperature between 45° C. and 160° C. to incorporate the drugs therein without damage caused by heat or chemical reactions, the matrix being formed of a substantially linear block copolymer which is a reaction product of a polydiorganosiloxane which forms "soft" segments in said reaction product and a diisocyanate which forms "hard" segments, said copolymer having a glass transition temperature between 45° C. and 160° C. said soft segments comprising from 80 to 99 percent by weight, based on the weight of said copolymer, the average molecular weight of the copolymer being between 15,000 and 500,000.

15 Claims, No Drawings

BLOCK COPOLYMER MATRIX FOR TRANSDERMAL DRUG RELEASE

BACKGROUND OF THE INVENTION

1. Field of the Invention

This invention relates to the controlled release of medications or active substances which are administered transdermally. More particularly, this invention relates to matrices which are solids, at ambient temperatures and body temperatures, which are useful for controlling the release of at least one drug or medication. The matrices have a relatively low glass transition temperature such that various drugs can be incorporated, without heat damage, by melting or softening the matrix composition and mixing the drug into the softened composition.

2. Description of the Prior Art

Matrices have hitherto been used as a drug reservoir component of transdermal drug delivery devices. Often gels or pastes of various compositions have been employed in such applications because of the difficulty of incorporating drugs into resinous or elastomeric materials and also because many elastomers lack the desired permeability to various drugs and medications. Such matrices in the past have often lacked sufficient cohesive strength to be used alone and thus they had to be covered by membranes designed to control the rate at which the medications are released into the skin of the patient. Generally an impermeable backing material covers the top of the composite structure, and a pressure sensitive adhesive applied over all or a portion of the bottom side of the composite to attach the drug delivery device to the skin of the patient. The medication permeates through the matrix that forms the drug containing reservoir, the membrane, if any, and the pressure sensitive adhesive, if the latter is positioned between the drug containing reservoir and the skin. The exposed surface of the pressure sensitive adhesive is generally covered by a release liner that is removed and discarded when the device is used.

A number of patents disclose the general concept of transdermal drug delivery devices. Representative of these are U.S. Pat. No. 3,598,122 to Zaffaroni, and U.S. Pat. No. 4,615,699 to Gale et al. Those patents disclose the use of silicone gels and similar substances as matrix compositions. Also, the use of elastomers has been suggested by incorporation of the drug into a prepolymer gum stock which is subsequently vulcanized, or by mixing the drug into a prepolymer along with a catalyst which promotes curing of the prepolymer at low temperatures. See, for example U.S. Pat. No. 4,435,180 to Leeper. The disadvantage of such systems is that the cure is not complete at the time the drug is incorporated into the composition, and the drug may therefore be deleteriously affected by either the vulcanizing temperatures, the prepolymer, which may contain reactive components that react with certain drugs, or the curing agent which may interact with some drugs. In the case of the latter interactions the drug inhibits the curing reaction in some cases, while the curing agent affects the efficacy of the drug in other cases.

Matrices formed of silicone rubber such as those disclosed in the prior art also tend to be insufficiently permeable to provide the desired release rate of a medication in the case of medications which are of an ionic, hydrophilic, or oleophobic nature. Hydrophobic silicone polymers are not preferred in such applications because of the limited permeability of ionic or hydrophilic drugs through the polymers which are of a hydrophobic nature.

U.S. Pat. No. 4,686,137, which issued to Ward and Riffle on Aug. 11, 1987, discloses the use as an additive in base polymers of polyurethane urea-silicone block copolymers consisting essentially of a "hard" segment that is preferably a polyurethane formed from the reaction of diphenylmethane diisocyanate with a diol, and a "soft" segment having both hydrophilic and hyrophobic portions. The hydrophobic portion of the soft segment can be a polymeric tetraalkylene oxide, such as polytetramethylene oxide, a polydialkylsiloxane, or a mixture of these two polymers, and the preferred hydrophilic segment is polyethylene oxide. These copolymers are combined with a base polymer, such as a polyurethane, and a suitable solvent to form films suitable for use as wound dressings or semipermeable membranes and as coating compositions for textile materials. There is no disclosure, however, of thermoplastic low temperature softening copolymers containing a major weight percentage of silicone segments, which would be desirable as a matrix or reservoir for a drug delivery device.

An objective of this invention is to provide materials for matrices that enable the migration therethrough of a variety of medications and which can be melted or softened to the extent that a drug can be admixed therein at relatively low temperatures, i.e., about 45° C. to 160° C., which temperature is low enough to avoid thermal damage to the drug. The matrices of the present invention are thermoplastic materials which do not require the presence of curing agents, prepolymers, or catalysts. By elimination of the need of using such agents which might themselves alter the rate of drug delivery or present either health hazards in addition to possibly impairing the efficacy of the medication being administered, a number of problems encountered with the prior art are eliminated. Also an important advantage in the ability to employ commercially feasible assembly methods in manufacture of drug delivery devices is attained.

SUMMARY OF THE INVENTION

The present inventors discovered that certain members of the broad class of segmented block copolymers are unique by virtue of 1) their high permeability to the ingredients of various mixtures of medications including those of a hydrophilic type, (2) their resistance to dissolving and/or degradation by ingredients of the medications, and (3) their ability to be fabricated into composite devices by softening or melting at relatively low temperatures (45° C. to 160° C.) for incorporation therein of a drug. The present copolymers comprise a hard segment which comprises an organic diisocyanate or optionally is derived from the reaction of an organic diisocyanate with a diol or diamine and a soft segment (or oligomer) containing at least one polydiorganosiloxane unit. Matrices formed from these copolymers are particularly useful for containing, and, if desired, for controlling the rate of release of drugs and medications to the skin of a patient to whom the desired drug is being administered. The matrices can also be used as a reservoir in conjunction with a rate controlling membrane in such types of drug delivery systems, all of which are known in the art. The materials of the present invention can be characterized as low strength rubbers or high strength gels.

Briefly summarized, the present invention provides, in a transdermal drug delivery system, which includes in combination: (a) an impermeable backing member; (b) a matrix containing a medicinally active ingredient; said matrix comprising a substantially linear thermoplastic block copolymer which is a reaction product of a polydiorganosiloxane having end groups, preferably amino functional groups, which are reactive with an isocyanate to form polyurethane or polyurethane urea linkages, which polydiorganosiloxane units form "soft" segments in said reaction product; and a diisocyanate which forms "hard" segments. Said copolymer has a glass transition temperature ($T_g$) between about 45° C. and 160° C., preferably between 50° C. and 100° C. and said soft segments comprise from about 80 to 99 percent by weight, based on the weight of said copolymer, the average molecular weight of said soft segments being between 1200 and 30,000. Chain extenders, such as low molecular weight alkylene diols or diamines, can optionally be included in the polymer. Also optionally, polyalkylene oxides can be incorporated into the polymer to increase its hydrophilicity, thereby improving the permeability of the polymer as to hydrophilic or ionic drugs.

DETAILED DESCRIPTION OF THE INVENTION

This invention provides an matrix material for forming a drug-containing reservoir for use in transdermal drug delivery devices in which the matrix comprises a layer of a solid thermoplastic, linear, segmented copolymer having a glass transition temperature between about 45° C. and 160° C. where said layer is inert with respect to and permeable with respect to said drug or medication. The layer is a cohesive solid at ambient temperatures and is preferably about 0.05 to 5 mm. thick and is formed of a substantially linear segmented (block) copolymer comprising from about 1 to 20 weight percent of "hard" segments consisting essentially of polyurethane or polyurea units derived from an organic diisocyanate and, if desired, an alkylene diol or similar difunctional chain extender, and from 80 to 99 weight percent of "soft" segments comprising from 15 to 99 percent by weight, based on the weight of said copolymer, of a hydrophobic portion consisting essentially of one or more polydiorganosiloxane units. In the case of a hydrophilic drug, from 0 to 65 percent by weight, based on the weight of said copolymer, of a hydrophilic portion consisting essentially of at least one polyalkylene oxide unit, preferably polyethylene oxide (PEO), can be included in the polymer chains.

This invention also provides an improved method for forming a matrix for a drug delivery device, which comprises admixing a drug into a molten or softened copolymeric material at temperatures which do not cause thermal damage to the drug, and then cooling the resultant composition to form the drug-containing matrix. In many cases the composition will soften sufficiently to incorporate a drug therein at a temperature below the glass transition temperature, thus avoiding thermal damage to drugs even where the $T_g$ is fairly high. The composition can be formed into matrices of the desired size either by casting directly from the softened state or cutting from a sheet of the composition formed by cooling the mixture. The rate-controlling element for releasing the medicinal ingredients from the drug-containing reservoir of a drug delivery device may be the material of the matrix or composite devices can be formed in which a rate controlling membrane can be positioned over the matrix which acts as a reservoir.

The molecules of block copolymer that constitute the matrices of the present invention contain at least one segment of a "hard" polymer and at least one segment of a "soft" polymer. It is understood in the art that the terms "hard" and "soft" as applied to segments of block copolymers refer to the relative glass transition temperatures ($T_g$) of the segments. The hard segment has a higher glass transition temperature than the soft segment.

The hard segment of the present polyurea or polyurethane copolymers is derived from an organic diisocyanate and, optionally, a low molecular weight diol or diamine, sometimes referred to as a chain extender. Any of the available aliphatic, aromatic or cycloaliphatic diisocyanates can be used to prepare the polyurea or polyurethane portion of these copolymers. Preferred diisocyanates include but are not limited to p-tolylene diisocyanate (TDI), 4,4'-diphenyl methane diisocyanate (MDI) and 4,4'-dicyclohexylmethyldiisocyanate ($H_{12}MDI$), and isophorone diisocyanate (IPDI).

The chain extender portion of the polyurethane can be any of the available aliphatic diols or diamines containing from 2 up to about 10 carbon atoms. Diols containing from 2 to 4 carbon atoms are preferred, based on the availability and biocompatibility of these compounds.

The hard segment constitutes from about 1 to 20 weight percent of the copolymer, preferably from 3 to 15 weight percent, and the molar ratio of hard segment (diisocyanate and aliphatic diol units) to soft segments (polydiorganosiloxane and polyoxyalkylene units) is from 1:1 to 4:1. The soft segment of the present copolymers may include a hydrophilic and a hydrophobic portion. The hydrophobic portion of the copolymer molecules consists essentially of at least one sequence of from 15 to about 400 diorganosiloxane units, and these sequences constitute from 15 to 99 weight percent, preferably from 40 to 97 weight percent, of the copolymer. The preferred polydiorganosiloxane is polydimethlysiloxane (PDMS), because of its biocompatibility, high drug permeability, and commercial availability. Methods for preparing functionally substituted polydiorganosiloxanes and copolymerizing these polymers with diisocyanates and other organic monomers are known in the art and do not form part of this invention. See for example, Gornowicz et al U.S. Pat. No. 4,631,629. The preferred method is, however, the reaction in a suitable solvent of a diamino terminated diorganosiloxane oligomer with an approximately stoichiometric amount of an organic diisocyanate. The mixture is then reacted with a quantity of a low molecular weight alcohol, such as ethanol to make certain that there are no unreacted isocyanate groups remaining in the mixture.

The hydrophilic portion of the soft segment consists essentially of at least one sequence per copolymer molecule of from 5 to 75 ethylene oxide units, which can be present as part of the linear portion of the copolymer. The alkylene oxide units, which are preferably ethylene oxide units constitute from 0 to 65 weight percent of the copolymer.

The optimum molecular weight range for a given copolymer will be determined by the desired physical properties of the copolymer, such as melt viscosity, tackiness, and particularly the glass transition temperature of the hard segment of the copolymer. The weight average molecular weight is preferably from 15,000 to about 500,000, preferably 25,000 to 300,000. If a matrix for drug release is prepared from a thermoplastic copolymer of this invention, the weight average molecular weight of the copolymer is typically in the range of from 25,000 to about 300,000 to provide copolymers which melt (or soften to a degree sufficient to permit drug admixture) at temperatures which are in the range of about 45° C. to 160° C.. The preferred softening temperature in each case is dependant on the heat sensitivity of the particular drug incorporated into the matrix.

The specific drugs used are not critical to this invention and as used herein the term "drug" is to be construed in its broadest sense as a material which is intended to produce some beneficial effect on the organism to which it is applied. As used herein, a drug in its acid or basic form is considered to be oleophobic if the solubility of the drug in mineral oil is less than about 100 mg/g. A drug is considered to be "highly polar" when the percent ionization of the drug in an aqueous drug reservoir is at least about 95%. This occurs when the pKa of the drug differs from the pH of the reservoir by an absolute value of at least 1.3. The pKa of a drug is the pH of an aqueous solution in which 50% is in the unionized base or acid form. Since physiological pH of the skin is in the range of approximately 5.5–7.2; the pKa for acidic drugs according to this invention is lower than about 4.2 and for basic drugs, higher than 8.5. Representative drugs meeting these criteria include, without limitation, acidic drugs such as the sodium or other salts of indomethacin, methazolamide, and acetylsalisylic acid, for example. Other drugs which can be incorporated into matrices of this invention include phenylephrine, chlorpheniramine, phenylpropanolamine, clonidine, and propranolol.

Methods for preparing diorganosiloxane/polyurethane urea-oxyethylene copolymers are described in patents and other literature, see for example, Tyagi et al, "Segmented organosiloxane copolymers", *Polymer*, Vol. 25, pp 1807–1816. In accordance with a preferred method a liquid amino functional polydiorganosiloxane containing from 15 to about 100 repeating units per molecule and a monofunctional isocyanate-reactive group such as

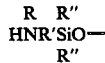

at the two terminal positions is reacted with the organic diisocyanate by heating the mixture in the presence of a suitable catalyst. Other isocyanate reactive groups which can be substituted include HOR'Si— and HSR'Si—. In the foregoing the aliphatic diol that optionally forms part of the hard segment is then added to the reaction mixture and heating continued until all of the isocyanate is reacted, which typically takes an additional 2 to 16 hours. The reaction is preferably conducted under an inert atmosphere such as nitrogen using as the reaction medium one or more organic liquids such as toluene, tetrahydrofuran (THF), or dimethylformamide (DMF) or mixtures of such solvents that will dissolve all of the reactants and the resultant copolymer.

The substituents represented by R and R" in the preceding formula are monovalent hydrocarbon radicals and R' represents an alkylene radical. Each of the R, R', and R" radicals may be the same or different.

The present block copolymers are thermoplastic and can be processed to form layers using any of the known techniques for fabricating thermoplastic organic polymers. These techniques include but are not limited to pressing, calendaring, and extrusion of bulk copolymers and dissolving the copolymers to form solutions that are then applied to a suitable substrate to form coatings.

The following examples describe preferred embodiments of the present invention. The examples should not be interpreted as restricting the scope of the invention as defined in the accompanying claims. Unless otherwise specified, all parts and percentages in the examples are by weight.

EXAMPLE 1 - COPOLYMER PREPARATION

Urea copolymers were prepared as follows: $H_{12}MDI$ (53 g, 0.398 eq) and dry toluene (1450 g) was added to a 3 liter, 3 neck flask equipped with an air stirrer, heating mantel, reflux condenser, addition funnel and nitrogen atmosphere. N-Methylamino-iso-butyl end blocked PDMS (1397.2 g, 0.398 eq) was added dropwise. After all the siloxane had been added, the reaction was stirred for 1 hour at room temperature and then poured into glass baking dishes. Most of the toluene was allowed to evaporate in a hood. Residual toluene was then removed in a vacuum oven to give pure Copolymer C in Table I. A slight excess of isocyanate can be used to make sure all the amine end blocked PDMS is reacted. This gives copolymers with isocyanate ends which are quenched with excess ethanol before removing the solvent.

EXAMPLE 2

The other urethane-urea copolymers listed in Table I were prepared in a similar manner. A catalyst, usually a tin salt or amine, is necessary to effect the reaction of carbinols with aliphatic isocyanates. An example of an urethane-urea copolymer preparation is as follows. PEO (127.7 g, 0.167 eq) and toluene (500 g) were put in a 3 liter, 3 neck flask equipped with an air stirrer, Dean Stark trap, nitrogen atmosphere and reflux condenser. PEO was dried by azeotroping the water with toluene at reflux for 1 hour. Solution was cooled to 30° C. The Dean Stark trap was removed and an addition funnel and temperature controller were attached to the flask. $H_{12}MDI$ (33.3 g, 0.25 eq) was added to the flask. A solution of N-Methylamino-iso-butyl end blocked PDMS (303.8 g, 0.083 eq) in toluene (584.5 g) was added slowly. Dibutyltin dilaurate (DBTDL) (0.3 ml of 10% solution in toluene) was added and the reaction was heated at 100° C. overnight. The solution was poured into a baking dish and the toluene was removed in a vacuum oven at 80° C. to give Copolymer F.

EXAMPLE 3

The following examples illustrate the use of chain extenders in making the desired copolymers. $H_{12}MDI$ (26.6 g, 0.2 eq) and toluene (460 g) were put in a 3 liter, 3 neck flask equipped with an air stirrer, heating mantel, reflux condenser, addition funnel and nitrogen atmosphere. N-methylamino-iso-butyl end blocked PDMS (100 dp), (366 g, 0.1 eq) in toluene (460 g) was added slowly. 1,3-Butanediol (4.5 g, 0.1 eq) and DBTDL (0.3 ml of 10% solution in toluene) were added and the reaction heated at 100° C. overnight. Solvent was removed in a vacuum oven at 80° C. to give Copolymer G.

EXAMPLE 4

Using a similar procedure as above, $H_{12}MDI$ (43.3 g, 0.325 eq, 12.3%) was reacted with a 50 dp N-methylamino-iso-butyl end blocked PDMS (213.5, 0.13 eq, 60.7%) and PEO 1540 (91.7 g, 0.12 eq, 26.1%) using DBTDL (0.3 ml of 10% solution in toluene). Reaction was heated 1 hour at 100° C. Then, 1,4-butanediol (3.4 g, 0.075 eq, 1.0%) was added. Reaction was heated overnight. Solution was poured into baking dishes and most of the solvent was allowed to evaporate in a hood. Residual solvent was removed in a vacuum oven to give Copolymer H.

EXAMPLE 5

Copolymer C was heated in beakers at 110° C. and various amounts of drugs, or drugs in an excipient such as isopropylpalmitate (IPP), were added and the mixture was stirred with a spatula until homogeneous.

The melts were poured into a hop plate/chase and allowed to cool to room temperature giving 1.9 mm thick slabs of copolymer containing dispersed drugs. Disks, 2 cm. in diameter, were cut from the slab and drug release rates were measured, using the Vander-Kamp 600 Dissolution System (Model 10948 Vander-Kamp® 600, Van-Kel Industries, Inc.). The experimental conditions are shown below: Receptor solution: 40% PEG 400, a 400 molecular weight PEO, and 60% water.

Rotation speeed: 425 rpm.
Temperature: 37° C.
Time course: 24 hours.

The amount of drug release was plotted against the square root of time to give a straight line from which the release rate was calculated. Results are summarized in Table II.

EXAMPLE 6

Various drugs were mixed with copolymers A-H, either as described in Example 1, or in a heated mixer, Haake Buchler Rheocord System 40. About 60 grams of drug and copolymer, ratio of each varied depending on the desired loading of drug in the final matrix, were loaded into the mixer and mixed at 60°–100° C. The molten mixture was removed and allowed to cool to room temperature. The integrity and the dynamic viscosity of the resulting drug matrix are reported in Table II.

TABLE I

| | Composition and properties of thermoplastic silicones. | | | | | | |
|---|---|---|---|---|---|---|---|
| Copolymer | Weight % PDMS | Weight % PEO | Weight % Diisocyanate | Weight % Chain Extender | Durometer (Shore A)[1] | GPC Mw[2] | Tg deg. C. |
| A | 81 | 0 | 19 | 0 | 78 | 257,000 | 54 |
| B | 89.2 | 0 | 10.8 | 0 | 57 | 100,000 | 59 |
| C | 96.5 | 0 | 3.5 | 0 | 30 | 150,000 | 65 |
| D | 98.7 | 0 | 1.3 | 0 | 3 | 202,000 | 45 |
| E | 96.6 | 0 | 3.4 | 0 | 11 | 104,000 | 130 |
| F* | 65.5 | 27.5 | 7 | 0 1,3-butanediol | 4 | 37,100 | 48 |
| G* | 92.2 | 0 | 6.7 | 1.1 1,4-butanediol | 27 | 39,600 | 56 |
| H* | 60.7 | 26.1 | 12.3 | 1 | 29 | 34,200 | 53 |

[1]Durometer was tested in accordance with ASTM D2240-86
[2]Gel permeation chromotography (GPC) for copolymers C & D was run in toluene at 2 ml/min using PDMS calibration standards
GPC for other copolymers was run in tHF at 2 ml/min using polystrene calibration standards
*DBTDL catalyst was used

TABLE II

Release of drugs from thermoplastic silicone matrix (Copolymer C).

| Drug/excipient | Loading Level Weight % | Release Rates (micrograms/cm² hr) |
|---|---|---|
| Progesterone | 1 | 171 |
| Progesterone | 5 | 328 |
| Progesterone | 10 | 521 |
| Progesterone/10% IPP | 10 | 626 |
| Indomethacin | 1 | 14 |
| Indomethacin | 5 | 59 |
| Indomethacin | 10 | 103 |
| Indomethancin/10% IPP | 10 | 118 |

TABLE III

Properties of thermoplastic silicones as drug matrices.

| Copolymer | Drug | Weight % Drug | Matrix Integrity | Dynamic Viscosity 25° C. 100 radians/sec Pa.s |
|---|---|---|---|---|
| A | Indomethacin | 10 | E | 24,200 |
| B | Cimetidine | 10 | E | 23,200 |
| C | Progesterone | 5 | G | 7,150 |
| C | Indomethacin | 10 | G | 5,640 |
| C | Hydrocortisone | 5 | G | 7,220 |
| C | Cineole | 10 | G | 3,890 |
| C | Methylsalicylate | 10 | G | 2,330 |
| C | Chlorphenirameine[a] | 9.6 | G | 3,400 |
| C | Propranolol | 10 | E | 6,980 |
| C | Aminophylline | 10 | E | 6,790 |
| C | Nicotine[b] | 10 | S | 1,050 |
| D | Indomethacin | 10 | S | 20,700 |
| E | Propranolol | 10 | S | 2,110 |
| F | Indomethacin | 10 | S | 2,700 |
| G | Indomethacin | 10 | G | 4,460 |
| H | Hydrocortisone | 10 | G | 6,530 |

[a]Chlorpheniramine was absorbed on fumed silica then mixed into the molten copolymer.
[b]Nicotine was dispersed with Methocel and water then mixed into the molten copolymer.
In the foregoing "E" means excellent, "G" means good, "S" means satisfactory That which is claimed is:

1. In a transdermal drug delivery system, comprising in combination:
   (a) an impermeable backing member;
   (b) a matrix containing a medicinally active ingredient; and,
   (c) means to attach said system to the skin of a patient; the improvement which comprises:
   said matrix comprising a substantially linear thermoplastic block copolymer which is a reaction product of a polydiorganosiloxane which forms soft segments in said reaction product and a diisocyanate which forms hard segments, said copolymer having a glass transition temperature between about 45° C. and 160° C. said soft segments forming from about 80 to 99 percent by weight, based on the weight of said copolymer, said hard segments forming about 1 to 20 weight per cent, based on the weight of said copolymer, the average molecular weight of said copolymer being between about 15,000 and 500,000.

2. A device according to claim 1 where said copolymer contains a low molecular weight diol or diamine chain extender.

3. A device according to claim 1 wherein said matrix is in the form of a layer having a thickness of from 0.05 mm. to 5.0 mm.

4. A device according to claim 2 where the organic diisocyanate is p-tolylene diisocyanate, 4,4'-diphenylmethanediisocyanate, 4,4'-dicyclohexylmethanediisocyanate, or isophorone diisocyanate.

5. A device according to claim 1 wherein said copolymer has a glass transition temperature between 50° C. and 100° C.

6. An improved matrix for use as a drug containing and releasing reservoir in a transdermal drug delivery system which comprises a substantially linear block copolymer that is a reaction product of a polydiorganosiloxane which forms soft segments in said reaction product and a diisocyanate which forms hard segments therein, said copolymer having a glass transition temperature between about 45° C. and 160° C., said soft segments comprising from about 80 to 99 percent by weight, based on the weight of said copolymer, the average molecular weight of said polymer being between 15,000 and 500,000, and a drug dispersed in said matrix.

7. An improved method for forming a drug delivery matrix comprising
(A) selecting a polymeric material consisting substantially of a linear block copolymer comprising from 1 to 20 weight percent of hard segments consisting essentially of polyurethane units derived from an organic diisocyanate and an alkylene diol, and from 80 to 99 weight percent of soft segments comprising from 15 to 99 percent by weight, based on the weight of said copolymer, of polydiorganosiloxane units, based on the weight of said copolymer, said copolymer having a glass transition temperature between about 45° C. and 160° C.,
(B) heating said copolymer to a temperature sufficient to soften the same,
(C) admixing a drug into said softened copolymer, and
(D) cooling the resultant composition to harden the same.

8. A method according to claim 7 where said drug is of an hydrophilic character, and the hard segment of the copolymer constitutes from 1 to 20 percent by weight of the copolymer, the polydiorganosiloxane units which have an average molecular weight between about 1200 and 30,000.

9. A method according to claim 7 wherein said composition is formed into a layer having a thickness of from 0.05 to 5.0mm.

10. A method according to claim 8 where the organic diisocyanate is p-tolylene diisocyanate, 4,4'-diphenylmethanediisocyanate or 4,4'-dicyclohexylmethanediisocyanate, the alkylene diol is 1,4-butanediol, the polydiorganosiloxane units contain from 20 to 40 diorganosiloxane repeating units.

11. A method according to claim 7 wherein said soft segments comprise from 0 to 65 percent by weight, based on the weight of said copolymer, of a hydrophilic portion consisting essentially of at least one polyalkylene oxide unit.

12. A method according to claim 7 wherein the organic diisocyanate is p-tolylene diisocyanate, 4,4'-diphenylmethanediisocyanate or 4,4'-dicyclohexylmethanediisocyanate, and the alkylene diol is 1,4-butanediol, the polydiorganosiloxane units contain from 20 to 40 diorganosiloxane repeating units, the molar ratio of diisocyanate units to alkylene diol units and polydiorganosiloxane units is 1:1.

13. A method according to claim 11 wherein said polyalkylene oxide is polyethylene oxide.

14. A drug delivery system according to claim 1 wherein said polydiorganosiloxane comprises polydimethylsiloxane.

15. A method according to claim 7 wherein said polydiorganosiloxane comprises polydimethylsiloxane.

* * * * *